US006410590B1

(12) United States Patent
Nanduri et al.

(10) Patent No.: US 6,410,590 B1
(45) Date of Patent: Jun. 25, 2002

(54) COMPOUNDS HAVING ANTITUMOR ACTIVITY: PROCESS FOR THEIR PREPARATION AND PHARMACEUTICAL COMPOSITIONS CONTAINING THEM

(75) Inventors: Srinivas Nanduri; Sriram Rajagopal; Sairam Pothukuchi; Sunilkumar Bhadramma Kochunarayana Pillai; Ranjan Chakrabarti, all of Hyderabad (IN)

(73) Assignee: Dr. Reddy's Research Foundation, Andhra Pradesh (IN)

(*) Notice: Subject to any disclaimer, the term of this patent is extended or adjusted under 35 U.S.C. 154(b) by 0 days.

(21) Appl. No.: 09/775,533

(22) Filed: Feb. 1, 2001

(30) Foreign Application Priority Data

Feb. 3, 2000 (IN) ..................................... 089/MAS/2000

(51) Int. Cl.$^7$ .................... A61K 31/341; C07D 307/42; C07D 307/46
(52) U.S. Cl. ...................... 514/462; 514/473; 549/264; 549/313; 549/320
(58) Field of Search ................................ 549/313, 320, 549/264; 514/462, 473

(56) References Cited

FOREIGN PATENT DOCUMENTS

| JP | 6388124 | 4/1988 |
|----|---------|--------|
| WO | 9101742 | 2/1991 |
| WO | 9617605 | 6/1996 |

OTHER PUBLICATIONS

Basak, A. et al., "Inhibition of Proprotein Convertases–1, –7 and Furin by Diterpines of *Andrographis paniculata* and Their Succinoyl Esters" Biochemistry Journal, vol., 338, p. 107–113, (1999).
Chang, R.S. et al. "Dehydroandrographolide Succinic Acid Monoester as an Inhibitor Against the Human Immunodeficiency Virus" Proc. Soc. Exp. Biol. Med., vol. 197, p. 59–66, (1991).
Matsuda, T. et al. "Cell Differentiation–Inducing Diterpenes from *Andrographis paniculata* Nees" Chem. Pharm. Bull. vol. 42 (6), p. 1216–1225, (1994).
Siripong, P. et al. "Cytotoxic Diterpenoid Constituents From *Andrographis paniculata* Nees Leaves" J. Sci. Soc. Thailand, vol. 18, p. 187–194, (1992).
Choudhury, B.R. et al. "In Vivo and In Vitro Effects of Kalmegh (*Andrographis paniculata*) Extract and Andrographolide on Hepatic Microsomal . . . Enzymes" Planta Medica, vol. 53 (2), p. 135–140, (1987).
Puri, A. et al. "Immunostimulant Agents from *Andrographis paniculata*" Journal of Natural Product, vol. 56 (7), p. 995–999, (1993).
Rahman, N.N.N.A. et al. "Antimalarial Activity of Extracts of Malaysian Medicinal Plants" Journal of Ethanopharmacology, vol. 64, p. 249–254, (1999).
Misra, P. et al. Antimalarial Activity of *Andrographis paniculata* (Kalmegh) against *Plasmodium berghei* NK 65 in *Mastomys natalensis*, Int. J. Pharmacog., vol. 30 (4), p. 263–274, (1992).
Long, D.W. "Antiinfammatory Agents from Traditional Chinese Drugs" Drugs of the Future, vol. 15 (8), p. 809–816, (1990).
"The Useful Plants of India" Ed. S.B. Ambasta, p. 39, (1992).
"Glossary of Indian Medicinal Plants" Ed. R.N. Chopra et al. p. 18, (1956).
Gupta, S. et al. "Antidiarrhoeal Activity of Diterpenes of *Andrographis paniculata* (Kal–Megh) Against *Escherichia coli* Enterotoxin in in vivo Models" Int. J. Crude Drug Res., vol. 28 (4), p. 273–283, (1990).
Medicinal & Aromatic Plants Abstracts, Wang, D.W. et al. Chinese Medical Journal, vol. 107 (6), p. 464–470, (1994).
Medicinal & Aromatic Plants Abstracts, Zhao, H. Y. et al. Chinese Medical Journal, vol. 104 (9), p. 770–775, (1991).
American Chemical Society, Meijer, L. Prog. Cell Cycle Research, vol. 1, p. 351–363, (1995).
Pharmaceutical Chemistry, K. Gorter, Rec. Trav. Chim. vol. 30, p. 151–160, (1911).
Cava, M.P. et al. "The Structure of Andrographolide" Tetrahedron, p. 397, (1962).

*Primary Examiner*—Ba K. Trinh
(74) *Attorney, Agent, or Firm*—Ladas & Parry

(57) ABSTRACT

The present invention relates to novel derivatives of Andrographolide, their stereoisomers, their polymorphs, their pharmaceutically acceptable salts, and their pharmaceutically acceptable solvates. The novel derivatives of Andrographolide have the general formula (I)

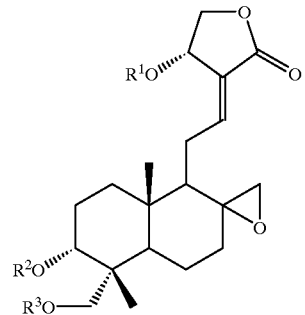

The andrographolide derivatives represented by general formula (I) are useful for treating cancer, HSV, HIV, psoriasis, restonosis, atherosclerosis, other cardiovascular disorders, and can be used as antiviral, antimalarial, antibacterial, hepatoprotective, and immunomodulating agents and for treatment of other metabolic disorders.

27 Claims, No Drawings

COMPOUNDS HAVING ANTITUMOR ACTIVITY: PROCESS FOR THEIR PREPARATION AND PHARMACEUTICAL COMPOSITIONS CONTAINING THEM

FIELD OF THE INVENTION

The present invention relates to novel anticancer agents, their stereoisomers, their polymorphs, their pharmaceutically acceptable salts, and their pharmaceutically acceptable solvates. The present invention more particularly relates to novel derivatives of Andrographolide, their stereoisomers, their polymorphs, their pharmaceutically acceptable salts, and their pharmaceutically acceptable solvates. The novel derivatives of Andrographolide have the general formula (I),

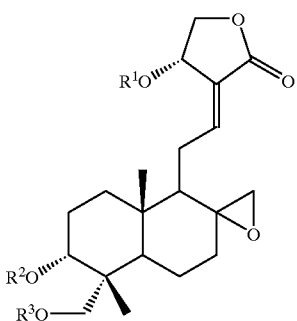

I where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, sulfonyl group or a group —(CO)—W—$R^4$ where W represents O, S, or $NR^5$, wherein $R^5$ represents hydrogen or ($C_1$–$C_6$) alkyl group, $R^4$ represents substituted or unsubstituted groups selected from alkyl, aryl, aroyl, or aralkyl or $R^2$ and $R^3$ together form a substituted or unsubstituted 3 to 7 membered cyclic structure containing carbon and oxygen atoms.

The andrographolide derivatives represented by general formula (I) defined above of the present invention are useful for treating cancer and other proliferative diseases including but not limited to herpes simplex virus types I and II, (HSVI and HSVII) and human immunodeficiency virus (HIV). The compounds of the present invention are also useful in the treatment of psoriasis, restonosis, atherosclerosis and other cardiovascular disorders. The compounds of the present invention are also useful as antiviral, antimalarial, antibacterial, hepatoprotective, immunomodulating agents and for treatment of metabolic disorders. The anticancer activity exhibited may be through cytotoxic activity, antiproliferation, cell cycle kinase inhibition or may be through cell differentiation.

The compounds of formula (I) are also useful for the treatment and/or prophylaxis of insulin resistance (type II diabetes), leptin resistance, impaired glucose tolerance, dyslipidemia, body weight reduction, disorders related to syndrome X such as hypertension, obesity, insulin resistance, coronary heart disease and other cardiovascular disorders.

The present invention also relates to pharmaceutical compositions containing compounds of general formula (I) or mixtures thereof.

The present invention also relates to a process for the preparation of the above defined compounds of general formula (I), their stereoisomers, their polymorphs, their pharmaceutically acceptable salts, and their pharmaceutically acceptable solvates.

BACKGROUND OF THE INVENTION

The plant *Andrographis paniculata* is extensively used in traditional medicine as a bitter tonic, febrifuge and in bowel complaints (*Glossary of Indian Medicinal Plants.*, Ed. R. N. Chopra, S. L. Nayar, I. C. Chopra, p18, 1996; *The useful plants of India*, Ed. By S. B. Ambasta, p39, 1992). The plant is useful in the treatment of bacterial infections (*Int. J. Crude Drug Res.* 1990, 28(4), p273–283; *Drugs of the Future.* 1990, 15(8) p809–816). It is reported to possess antimalarial (*Int. J. Pharmacognosy,* 1992, 30(4), p263–274; *J. Ethnopharmocol.,* 1999, 64(3), p249–254) and immunostimulant activity (*J. Nat. Prod.,* 1993, 56(7), p995–999). The plant has also been shown to be antithrombotic (*Chinese Medical Journal* 1991, 104(9), p770–775) and inhibit stenosis and restenosis after angioplasty in the rat (*Chinese Medical Journal,* 1994, 107(6), p464–470). It is also known that the plant extract and its constituents exhibit promising hepatoprotective activity (*Planta Medica,* 1987, 53(2), p135–140). Significant attention has been paid by several research groups on *A. paniculata* in recent years due to its cytotoxic, antitumorogenic, cell differentiation inducing activities and anti-HIV activities.

Andrographolide having the formula (II),

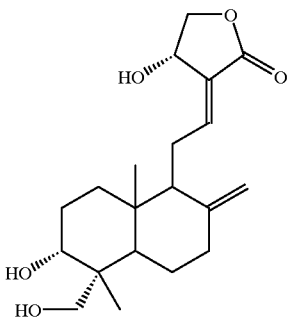

II the major constituent of the plant *A. paniculata* was first isolated by Gorter (Rec. *trav. chim.,* 1911, 30, p151–160).

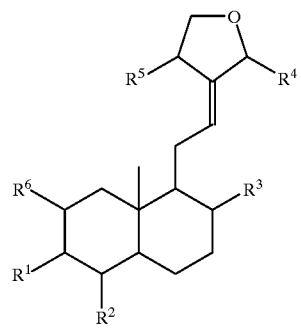

III

The extracts of the dried plant, which contain compounds of formula (III), have been assayed for the ability to decrease expression and phosphorylation of $p34^{cdc2}$ kinase, cyclin B and c-Mos for treating or preventing pathogenecity of diseases such as AIDS, Alzheimer's disease and hepatitis (WO 96/17605).

Cell cycle kinases are naturally occurring enzymes involved in regulation of the cell cycle (*Progress in Cell*

Cycle Research, 1995, 1, p351–363). Typical enzymes include the cyclin-dependent kinases (cdk) cdk1, cdk2, cdk4, cdk5, cdk6 and wee-1 kinase. Increased activity or temporarily abnormal activation of these kinases has been shown to result in development of tumors and other proliferative disorders such as restenosis. Compounds that inhibit cdks, either by blocking the interaction between a cyclin and its kinase partner or by binding to and inactivating the kinase, cause inhibition of cell proliferation and are thus useful for treating tumors or other abnormally proliferating cells.

The extract of A. paniculata was found to show significant cytotoxic activity against KB and P388 cells. Interestingly, Andrographolide of the formula II, has been shown for the first time to have potent cytotoxic activity against KB as well as P388 lymphocytic leukemia, where as 14-deoxy-11,12-didehydroandrographolide and neoandrographolide having the formulae IV & V

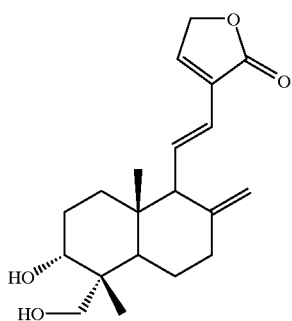

(IV)

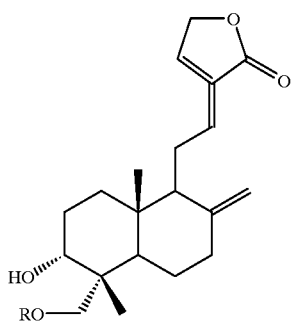

(V)

where R represents β-D-glucose moiety, have shown no cytotoxic activity in tumor cell lines (J. Sci. Soc. Thailand, 1992, 18, p187–194).

The methanolic extract of the aerial parts of A. paniculata Nees showed potent cell differentiation inducing activity on mouse myeloid leukemia (M1) cells (Chem. Pharm. Bull. 1994, 42(6) 1216–1225).

Japanese patent application JP 63-88124, discloses a mixture of at least two compounds of formula VIa and VIb,

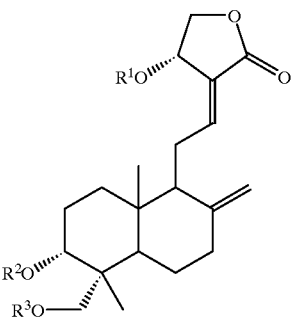

VIa

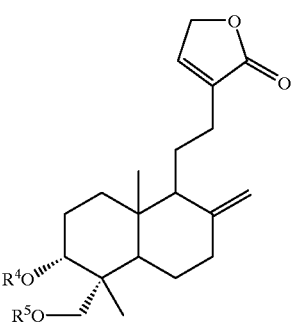

VIb where $R^1$, $R^2$, $R^3$, $R^4$ and $R^5$ represent hydrogen or lower alkanoyl group and their activity as antitumorogenic agents.

DASM (Dehydroandrographolide Succinic acid monoester) prepared from Andrographolide of the formula II is found to be inhibiting HIV virus and nontoxic to the H9 cell at the concentrations of 50–200 μg/ml and was inhibitory to HIV-1(IIIB) at the minimal concentration of 1.6–3.1 μg/ml (Proc. Soc. Exp. Biol. Med., 1991, 197, p59–66).

The plant Andrographis paniculata is also reported to inhibit proprotein convertases-1, -7 and furin possibly by suppressing the proteolytic cleavage of envelope glycoprotein gp 160 of HIV, which is known to be PC-mediated, particularly by furin and PC (Biochem. J., 1999, 338, 107–113)

In International patent application WO 91/01742, compositions containing one or more ingredients obtained from the plants Valeariana officinalis and/or A. paniculata were disclosed to have antiviral, antineoplastic, antibacterial and immunomodulatory activity.

Although several novel Andrographolide derivatives have been prepared, screened and reported in the above said prior-art literature for their anticancer activity, they are not showing interesting activity.

OBJECTIVE OF THE INVENTION

With an objective of preparing novel andrographolide derivatives useful for treating cancer, HSV, HIV, psoriasis, restonosis, atherosclerosis, cardiovascular disorders and as antiviral, antimalarial, antibacterial, hepatoprotective, immunomodulating agents and for treatment of metabolic disorders, which are potent at lower doses and having better efficacy with lower toxicity, we focussed our research efforts in preparing the novel Andrographolide derivatives of the formula (I) as defined above.

The main objective of the present invention is, therefore, to provide novel Andrographolide derivatives of the formula (I) as defined above, their stereoisomers, their polymorphs, their pharmaceutically acceptable salts, their pharmaceutically acceptable solvates and pharmaceutical compositions containing them or their mixtures.

Another objective of the present invention is to provide pharmaceutical compositions containing compounds of the formula (I), their stereoisomers, their polymorphs, their pharmaceutically acceptable salts, their pharmaceutically acceptable solvates, containing them or their mixtures in combination with suitable carriers, solvents, diluents and other media normally employed in preparing such compositions.

Still another objective of the present invention is to provide pharmaceutical compositions containing compounds of the formula (I), their stereoisomers, their polymorphs, their pharmaceutically acceptable salts, their pharmaceutically acceptable solvates, containing them or their mixtures in combination with one or more pharmaceutically acceptable active compounds with suitable carriers, solvents, diluents and other media normally employed in preparing such compositions.

Still another objective of the present invention is to provide a process for the preparation of Andrographolide derivatives of the formula (I) as defined above, their stereoisomers, their polymorphs, their pharmaceutically acceptable salts, their pharmaceutically acceptable solvates and pharmaceutical compositions containing them or their mixtures having enhanced activity with little or no toxic effect or reduced toxic effect.

DETAILED DESCRIPTION OF THE INVENTION

Accordingly, the novel derivatives of Andrographolide of the present invention have the general formula (I)

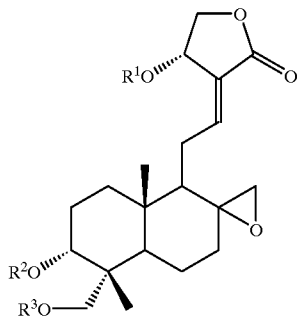

where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, sulfonyl group or a group —(CO)—W—$R^4$ where W represents O, S, or $NR^5$, wherein $R^5$ represents hydrogen or ($C_1$–$C_6$) alkyl group, $R^4$ represents substituted or unsubstituted groups selected from alkyl, aryl, aroyl, or aralkyl or $R^2$ and $R^3$ together form a substituted or unsubstituted 3 to 7 membered cyclic structure containing carbon and oxygen atoms; their stereoisomers, their polymorphs, their pharmaceutically acceptable salts and their pharmaceutically acceptable solvates.

Suitable groups represented by $R^1$, $R^2$ and $R^3$ include substituted or unsubstituted, linear or branched ($C_1$–$C_8$)alkyl group such as methyl, ethyl, n-propyl, iso-propyl and the like; aryl group such as phenyl, substituted phenyl and the like, the aryl group may be substituted; heteroaryl group such as pyridyl, furyl, thiophenyl and the like, the heteroaryl group may be substituted; aralkyl such as benzyl, phenethyl and the like, the aralkyl group may be substituted; heteroaralkyl group such as pyridylmethyl, pyridylethyl, furanmethyl, furanethyl and the like, the heteroaralkyl group may be substituted; ($C_2$–$C_8$) alkanoyl group such as ethanoyl, propanoyl, butanoyl and the like, the ($C_2$–$C_8$) alkanoyl group may be substituted; ($C_3$–$C_8$) alkenoyl group such as propenoyl, butenoyl, pentenoyl and the like, ($C_3$–$C_8$) alkenoyl group may be substituted; aroyl group such as benzoyl and the like, the aroyl group may be substituted; heteroaroyl group such as pyridyl carbonyl, furyl carbonyl and the like; the heteroaroyl group may be substituted; and sulfonyl group such as methanesulfonyl, benzenesulfonyl, p-toluenesulfonyl and the like, the sulfonyl group may be substituted.

The substituents on $R^1$, $R^2$ and $R^3$ may be selected from cyano, hydroxy, nitro, halogen atom such as fluorine, chlorine or bromine; substituted or unsubstituted group selected from ($C_1$–$C_8$)alkyl such as methyl, ethyl, propyl, butyl and the like, the substituents of ($C_1$–$C_8$)alkyl may be selected from halogen atom, hydroxy, nitro, cyano, amino, phenyl or ($C_1$–$C_6$)alkoxy groups; amino, mono or disubstituted amino group, the substituents of the amino group may be selected from hydroxy or ($C_1$–$C_6$) alkoxy groups; alkanoyl group such as ethanoyl, propanoyl, butanoyl and the like; ($C_1$–$C_6$) alkoxy group such as methoxy, ethoxy, propyloxy, butyloxy and the like; aroyl group such as benzoyl and the like; acyloxy group such as acetyloxy, propanoyloxy, butanoyloxy and the like; aryl group such as phenyl, naphthyl and the like, the aryl group may be mono or disubstituted and the substituents may be selected from ($C_1$–$C_6$)alkyl, halogen atom, amino, cyano, hydroxy, nitro, trifluoroethyl, thio, thioalkyl, alkylthio and ($C_1$–$C_6$)alkoxy groups; heteroaryl group such as pyridyl, furyl, thienyl and the like; mono ($C_1$–$C_6$)alkylamino group such as $CH_3NH$, $C_2H_5NH$, $C_3H_7NH$, and $C_6H_{13}NH$ and the like; di($C_1$–$C_6$)alkylamino group such as $(CH_3)_2N$, $(C_2H_5)NCH_3$ and the like; acylamino groups such as $CH_3CONH$, $C_2H_5CONH$, $C_3H_7CONH$, $C_4H_9CONH$, and $C_6H_5CONH$; arylamino group such as $C_6H_5NH$, $(C_6H_5)NCH_3$, $C_6H_4(CH_3)NH$, $C_6H_4(Hal)NH$ and the like; aralkylamino group such as $C_6H_5CH_2NH$, $C_6H_5CH_2CH_2NH$, $C_6H_5CH_2NCH_3$ and the like; alkoxycarbonylamino group such as $C_2H_5OCONH$, $CH_3OCONH$ and the like; aryloxycarbonylamino group such as $C_6H_5OCONH$, $C_6H_5OCONCH_3$, $C_6H_5OCONC_2H_5$, $C_6H_4(CH_3)OCONH$, $C_6H_4(OCH_3)OCONH$, and the like; aralkoxycarbonylamino group such as $C_6H_5CH_2OCONH$, $C_6H_5CH_2CH_2OCONH$, $C_6H_5CH_2OCON(CH_3)$, $C_6H_5CH_2OCON(C_2H_5)$, $C_6H_4(CH_3)CH_2OCONH$, $C_6H_4(OCH_3)CH_2OCONH$ and the like; or COOR, where R represents hydrogen or ($C_1$–$C_6$)alkyl groups.

When the aryl group is disubstituted, the two substituents on the adjacent carbon atoms may form a linking group such as —X—$CH_2$—Y—, or —X—$CH_2$—$CH_2$—Y—, where X and Y may be same or different and independently represent O, NH, S or $CH_2$.

When the groups represented by $R^1$, $R^2$ or $R^3$ are multisubstituted, the substituents present on the two adjacent carbons may form a linking group —X—$(CR^6R^7)_n$—Y— where $R^6$ and $R^7$ represent ($C_1$–$C_8$)alkyl such as methyl, ethyl and the like, X and Y may be same or different and independently represent C, O, S, or NH; and n=1 or 2.

Suitable groups represented by $R^4$ include substituted or unsubstituted ($C_1$–$C_6$)alkyl such as methyl, ethyl, n-propyl and the like; aryl group such as phenyl, substituted phenyl and the like, the aryl group may be substituted; aralkyl such as benzyl, phenethyl and the like, the aralkyl group may be substituted; and aroyl group such as benzoyl and the like, the aroyl group may be substituted. The substituents on the alkyl group, aromatic moiety of the aryl group, aralkyl group or aroyl group include halogen atom such as fluorine, chlorine, and bromine; amino group, cyano, hydroxy, nitro, trifluoroethyl, $(C_1-C_6)$alkyl, and $(C_1-C_6)$alkoxy.

Pharmaceutically acceptable salts forming part of this invention include salts of the carboxylic acid moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, and aluminum salts. Salts may include acid addition salts where appropriate which include, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to present invention include;

8,17-epoxy andrographolide;
3,14,19-triacetyl 8,17-epoxy andrographolide;
3,14,19-tripropionyl 8,17-epoxyandrographolide;
3,14,19-tris chloro acetyl 8,17-epoxy andrographolide;
8,17-epoxy andrographolide 3,19-acetonide;
14-methoxy 3,19-diacetyl 8,17-epoxy andrographolide;
14-cinnamoyl 3,19-dihydroxy 8,17-epoxy andrographolide;
14-cinnamoyl 3,19-dipropionyl 8,17-epoxy andrographolide;
14-[4'-methoxycinnamoyl]3,19-dipropionyl 8,17-epoxy andrographolide;
8,17-epoxy 14-[3',4'-dimethoxycinnamoyl]3,19-dipropionyl andrographolide;
14-[3',4'-methylene dioxy cinnamoyl]3,19-dipropionyl 8,17-epoxy andrographolide;
14-[N-Boc glycinyl]8,17-epoxy andrographolide;
14-[N-Boc glycinyl]3,19-dipropionyl 8,17-epoxy andrographolide;
19-trityl 8,17-epoxy andrographolide;
3-acetyl 8,17-epoxy Andrographolide;
3,14-diacetyl 8,17-epoxy Andrographolide;
14,19-diacetyl 8,17-epoxy Andrographolide;
3,14-dipropionyl 8,17-epoxy Andrographolide;
14-[4S,5R(N-1-butoxycarbonyl)-2,2-dimethyl-4-phenyl-5-oxazolidine]carbonyl-3,19-diacetyl-8,17-epoxy andrographolide; and
14-[2'-acetoxy-3'-N-acetylamino-3'-phenyl]propanoyl-3,19-diacetyl-3,17-epoxyandrographolide.

Cinnamoyl is propenoyl substituted by phenyl.

The present invention also provides a process for the preparation of novel derivatives of Andrographolide of the general formula (I) where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, sulfonyl group or a group —(CO)—W—$R^4$ where W represents O, S, or $NR^5$, wherein $R^5$ represents hydrogen or $(C_1-C_6)$alkyl group, $R^4$ represents substituted or unsubstituted groups selected from alkyl, aryl, aroyl, or aralkyl or $R^2$ and $R^3$ together form a substituted or unsubstituted 3 to 7 membered cyclic structure containing carbon and oxygen atoms, their stereoisomers, their polymorphs, their pharmaceutically acceptable salts and their pharmaceutically acceptable solvates, which comprises:

(i) epoxidising Andrographolide of the formula (II)

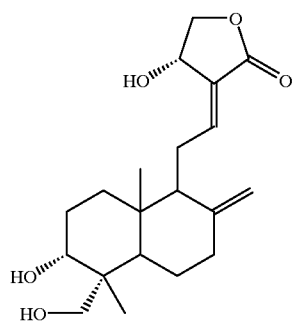

II by conventional methods to form a compound of formula (VII),

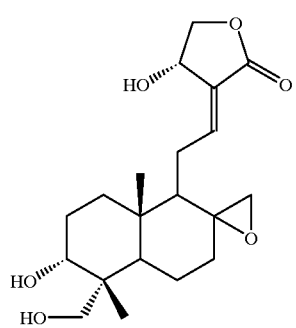

VII (ii) reacting the compound of formula (VII) with $R^1$—L, $R^2$—L and $R^3$—L, where $R^1$, $R^2$ and $R^3$ may be same or different and independently represent hydrogen or substituted or unsubstituted groups selected from alkyl, aryl, heteroaryl, aralkyl, heteroaralkyl, alkanoyl, alkenoyl, aroyl, heteroaroyl, sulfonyl group or a group —(CO)—W—$R^4$ where W represents O, S, or $NR^5$, wherein $R^5$ represents hydrogen or $(C_1-C_6)$alkyl group, $R^4$ represents substituted or unsubstituted groups selected from alkyl, aryl, aroyl, or aralkyl and L represents a leaving group such as hydroxy, halogen atom like fluorine, chlorine, bromine, or iodine; p-toluenesulfonate, methanesulfonate, trifluoromethanesulfonate, acyl group such as acetate, propanoate, butanoate and the like, to produce a compound of formula (I), and if desired, (iii) protecting the hydroxy groups present on carbons 3 or 19 or 3 and 19 together in the compound of formula (VII) with suitable protecting groups using conventional methods to produce a compound of formula (VIII),

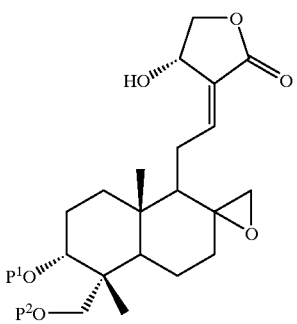

(VIII)

where $P^1$ and $P^2$ may be same or different and represent hydrogen, trityl, t-butyl dimethyl silyl, pivaloyl and the like, or esters such as acetate, propionate, benzoate and the like or together may form methylene dioxy, acetonide, benzilidine and the like, (iv) reacting the compound of formula (VIII) defined above with compound of formula (IX)

$$R^1—L \qquad (IX)$$

where $R^1$ and L have the meanings given above to produce a compound of formula (X),

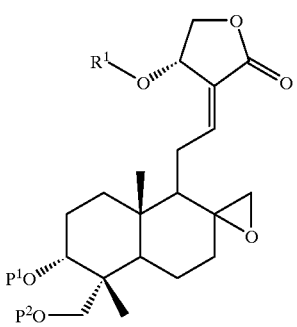

(X)

where $R^1$, $P^1$ and $P^2$ are as defined earlier, (v) deprotecting the compound of formula (X) by conventional methods to produce a compound of formula (XI),

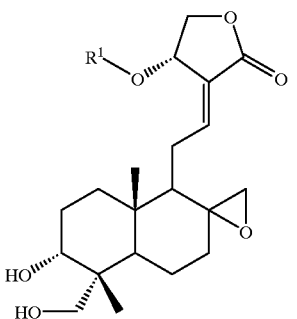

(XI)

where $R^1$ has the meaning given above, (vi) reacting the compound of formula (XI) where $R^1$ has the meaning given above with $R^2$—L and/or $R^3$—L, where $R^2$, $R^3$ and L are as defined above to produce a compound of formula (I), and if desired, (vii) converting compound of formula (I) into their stereoisomers, pharmaceutical salts or pharmaceutical solvates by conventional methods.

The epoxidation of a compound of formula (II) may be carried out in the presence of oxidising agents such as per acids which may selected from m-chloroperbenzoicacid, p-nitro perbenzoic acid, mono per phthalic acid, peroxy lauric acid, peroxy acetic acid, magnesium mono per phthalate; peroxides such as hydrogen peroxide of various strengths, t-butyl hydroperoxide and the like; iodine and bromine in presence of silver salts and other epoxidising agents such as N-chlorosuccinimide, N-bromosuccinimide, N-bromoacetamide, or dimethyl dioxirane may be used. During the epoxidation conventional solvents such as methanol, ethanol, chloroform, dichloromethane, tetrahydrofuran, dimethyl formamide (DMF), dioxane and the like or their mixtures may be used. The reaction may be carried out at a temperature in the range of −20° C. to 80° C., preferably in the range of −20° C. to 60° C.

The reaction of a compound of formula (VII) with $R^1$—L, $R^2$—L and $R^3$—L to produce a compound of formula (I) may be carried out in the presence of dicyclohexylcarbodiimide (DCC), diethyl azadicarboxylate (DEAD), diisopropyl azadicarboxylate (DLAD), ethyl chloro formate or the like. The reaction may be carried out in the absence or presence of a base selected from triethylamine, pyridine, dimethyl aminopyridine and the like. The reaction may also be carried out in the presence of an acid such as $H_2SO_4$, HCl, $HClO_4$, TFA, formic acid, Lewis acids like $BF_3$, $ZnCl_2$ etc. The reaction may be carried out in the presence of solvents such as dichloromethane, chloroform, $C_6H_6$, dimethyl sulfoxide, methanol, ethanol and the like or mixtures thereof. The reaction may be carried out at a temperature in the range of −70° C. to 200° C., preferably at a temperature in the range of −70° C. to 160° C. and the reaction time may range from 2 to 12 h, preferably from 2 to 10 h.

The protection of a compound of formula (VII) may be carried out using trityl chloride, t-butyldimethylsilyl chloride, pivaloyl chloride, dimethylsulfoxide, acetone, 2,2-dimethoxy propane, trimethyl ortho acetate, benzaldehyde, p-methoxy benzaldehyde, acetophenone and the like. The reaction may be carried out in the presence of a suitable catalyst such as $SOCl_2$, $H_2SO_4$, $HClO_4$, pyridinium p-toluene sulphonate, pyridine, p-toluene sulfonic acid, dimethyl aminopyridine, and the like. The reaction may be carried out in the absence or presence of suitable solvent such as benzene, DMF, dimethyl-sulfoxide (DMSO), acetonitrile, dichloromethane (DCM), and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The reaction of a compound of formula (VIII) with a compound of formula (IX) may be carried out in the presence of dicyclohexylcarbodiimide (DCC), diethyl azadicarboxylate (DEAD), diisopropyl azadicarboxylate (DIAD), ethyl chloro formate and the like. The reaction may be carried out in the absence or presence of a base selected from triethylamine, pyridine, dimethyl aminopyridine and the like. The reaction may also be carried out in the presence of an acid such as $H_2SO_4$, HCl, $HClO_4$, TFA, formic acid, and Lewis acids like $BF_3$, $ZnCl_2$ etc. The reaction may be carried out in the presence of solvents such as dichloromethane, chloroform, $C_6H_6$, dimethyl sulfoxide, methanol, ethanol and the like or mixtures thereof. The reaction may be carried out at a temperature in the range of −70° C. to 200° C., preferably at a temperature in the range of −70° C. to 160° C. and the reaction time may range from 2 to 12 h, preferably from 2 to 10 h.

The deprotection of a compound of formula (X) to produce a compound of formula (XI) may be carried out using deprotecting agent such as acetic acid, hydrochloric acid, formic acid, trifluoroacetic acid and the like. The reaction may be carried in the presence of suitable solvent such as water, THF, dioxane, DCM, $CHCl_3$, methanol and the like or mixtures thereof. The reaction may be carried out at a temperature in the range of 0° C. to 60° C., preferably at a temperature in the range of 20° C. to 40° C. The reaction time may range from 2 to 6 h, preferably from 2 to 4 h.

The reaction of compound of formula (XI) with $R^2$—L and/or $R^3$—L, to produce a compound of formula (I) may be carried out in the presence of dicyclohexylcarbodiimide (DCC), diethyl azadicarboxylate (DEAD), diisopropyl azadicarboxylate (DIAD), ethyl chloroformate and the like. The reaction may be carried out in the absence or presence of a base selected from triethylamine, pyridine, dimethyl aminopyridine and the like. The reaction may also be carried out in the presence of an acid such as $H_2SO_4$, HCl, $HClO_4$, TFA, formic acid, and Lewis acids like $BF_3$, $ZnCl_2$ etc. The reaction may be carried out in the presence of solvents such as dichloromethane, chloroform, $C_6H_6$, dimethyl sulfoxide, methanol, ethanol and the like or mixtures thereof. The reaction may be carried out at a temperature in the range of −70° C. to 200° C., preferably at a temperature in the range of −70° C. to 160° C. and the reaction time may range from 2 to 12 h, preferably from 2to 10 h.

The pharmaceutically acceptable salts are prepared by reacting the compounds of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. A mixture of solvents may be used. Organic bases like lysine, arginine, diethanolamine, choline, guanidine and their derivatives etc. may also be used. Alternatively, acid addition salts wherever applicable are prepared by treatment with acids such as hydrochloric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. A mixture of solvents may also be used.

The stereoisomers of the compounds of formula (I) forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like. Commonly used methods are compiled by Jaques et al in "Enantiomers, Racemates and Resolution" (Wiley Interscience, 1981).

Various polymorphs of the compounds of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or slow cooling. The presence of polymorphs may be determined by solid probe nmr spectroscopy, ir spectroscopy, differential scanning calorimetry, powder X-ray data or such other techniques.

Pharmaceutically acceptable solvates can be prepared by conventional methods such as dissolving the compounds of formula (I) in solvents such as water, methanol, ethanol etc., preferably water and recrystallizing by using different crystallization techniques.

The present invention also envisages pharmaceutical compositions containing compounds of the formula (I) defined earlier, their stereoisomers, their polymorphs, their pharmaceutically acceptable salts, their pharmaceutically acceptable solvates or their mixtures in combination with the usual pharmaceutically employed carriers, solvents, diluents and other media normally employed in preparing such compositions. The compositions may contain other active ingredients.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 25%, preferably 1 to 15% by weight of active compound, the remainder of the composition may be pharmaceutically acceptable carriers, diluents or solvents and may also contain other active ingredients.

The compounds of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

EXAMPLE 1

PREPARATION OF 8,17-EPOXY ANDROGRAPHOLIDE

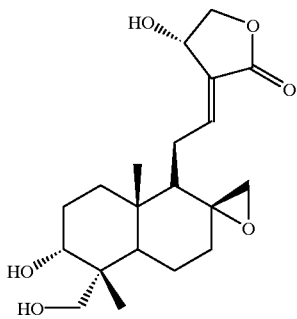

Andrographolide (500 mg) was dissolved in chloroform (50 ml with few drops of methanol) and to it was added meta chloro perbenzoic acid (980 mg) and the mixture stirred for 4 hours. The reaction was monitored by TLC. After completion of the reaction, the reaction mixture was concentrated and chromatographed over a column of silicagel (60–120 mesh; 50 grams) with chloroform acetone (75–25) as solvent system to obtain the title compound as a colourless solid (300 mg, 57%). m.p. 170° C.

$^1$H NMR: δ6.85 (1H, t, J=10 Hz, C-12 H), 5.00 (1H, d, J=5.8 Hz, C-14H), 4.40–4.00 (m), 3.40 (1H, t, C-3H), 3.25 (1H, d, C-19 Hb), 2.75 (2H, dd, J=12.4 Hz, C-17),

EXAMPLE 2

PREPARATION OF 3,14,19-TRIACETYL 8,17-EPOXY ANDROGRAPHOLIDE

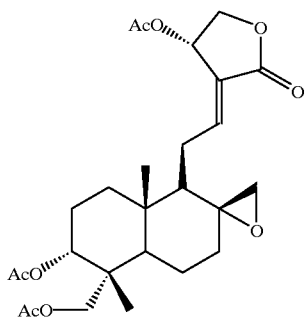

8,17-epoxy andrographolide (100 mg) obtained in Example 1 above was taken in 2 ml of acetic anhydride and refluxed for 5 minutes. The reaction was monitored by TLC. After completion of the reaction, the reaction mixture was diluted with solvent ether, washed with water and dried over $Na_2SO_4$ and concentrated. The residue obtained was chromatographed over a column of silicagel (60–120 mesh) with light petrol:ethyl acetate (65:35) as the solvent system to afford the title compound as a colourless solid (90 mg, 67%). mp: 195° C.

$^1$H NMR: δ7.09 (1H, t, J=10 Hz, C-12 H), 5.88 (1H, d, J=5.8 Hz, C-14 H), 4.55 (1H, C-3H), 4.5(1H, C-15Ha), 4.29(1H,C-19Ha), 4.21 (1H, C-15 Hb), 4.16(1H, C-19Hb), 2.6(2H, dd, J=12,4 Hz, C-17H), 2.11 (3H, S, OAc), 2.05(6H, s, OAc)

EXAMPLE 3

PREPARATION OF 3,14,19-TRIPROPIONYL 8,17-EPOXYANDROGRAPHOLIDE

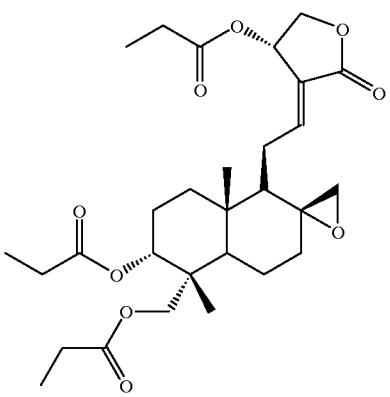

8,17-epoxyandrographolide (200 mg) obtained in Example 1 was taken in propionic anhydride (3 ml) and the mixture was refluxed for 5 minutes. The reaction was monitored by TLC. After completion of the reaction, the reaction mixture was poured into water (50 ml) and extracted with dichloromethane. The organic layer was dried over $Na_2SO_4$ and concentrated. The concentrated residue was recrystallised with ethanol to yield the title compound as colourless solid (115 mg, 39%) m.p. 119° C.

$^1$H NMR: δ7.1 (1H, t, J=10 Hz, C-12 H), 5.9 (1H, d, J=5.8 Hz, C-14 H), 4.7–4.5 (m), 4.4 –4.0 (m), 2.6 (2H, dd, J=12, 4 Hz, C-17 H), 2.5 –2.3 (m, Propyl)

EXAMPLE 4

PREPARATION OF 3,14,19-TRIS CHLORO ACETYL 8,17-EPOXY ANDROGRAPHOLIDE

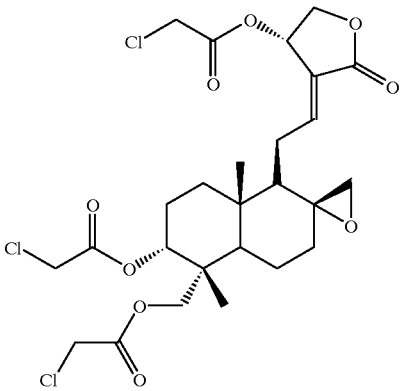

8,17-epoxy andrographolide (400 mg) obtained in Example 1, chloro acetic acid (770 mg), dicyclohexylcarbodiimide (1.6 gms) and triethyl amine (1 ml) were taken in dichloromethane (20 ml) and the mixture stirred for 1 hour at room temperature. The reaction was monitored by TLC. After completion of the reaction, the reaction mixture was filtered to remove the insoluble urea, diluted with dichloromethane, washed with saturated $NaHCO_3$ and water successively. The organic layer was dried over $Na_2SO_4$ and concentrated. The residue obtained was chromatographed over a column of silicagel (60–120 mesh) with chloroform:acetone (98:2) as the eluent to yield the title compound as a colourless solid (200 mg, 31%) m.p 180° C.

¹HNMR: δ7.1 (1H, t, J=10 Hz, C-12 H), 6.0 (1H, d, J=5.8 Hz, C-14 H), 4.7–4.5 (m), 4.4–4.0 (m), 2.6 (2H, dd, J=12, 4 Hz, C-17 H).

EXAMPLE 5

PREPARATION OF 8,17-EPOXY ANDROGRAPHOLIDE 3,19-ACETONIDE

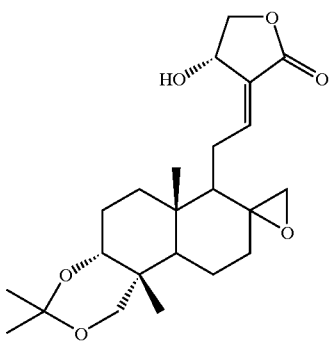

8,17-epoxy andrographolide (2 g) was taken in a mixture of 2,2-dimethoxy propane (15 ml) and DMSO (2 ml). The mixture was heated to about 45° C. until a clear solution was obtained. Then the solution was cooled to room temperature, a catalytic amount of pyridinium p-toluene sulphonate (PPTS) was added and the contents were stirred for one hour at room temperature. After the reaction was completed, the reaction mixture was quenched with triethylamine (2 ml), poured into water (100 ml), extracted with DCM (3×200 ml). The organic layer was dried over sodium sulfate and concentrated to dryness. The residue was chromatographed over a column of silicagel with chloroform:acetone (95:5) as the eluent to obtain 8,17-epoxy andrographolide 3,19-acetonide (2 g, 90%). m.p: 179° C.

¹H NMR: δ6.8 (1H, m, C-12), 5.0 (1H, d, C-14), 4.4–4.0 (m), 3.95 (1H, d, C-19Ha), 3.55 (1H, dd, C-33), 3.2 (1H, d, C-19 Hb), 2.8 (2H, dd, J=12, 4 Hz, C-17 H), 1.4 (3H, s) and 1.35 (3H, s) (Acetonide).

EXAMPLE 6

PREPARATION OF 14-METHOXY 3,19-DIACETYL 8,17-EPOXY ANDROGRAPHOLIDE

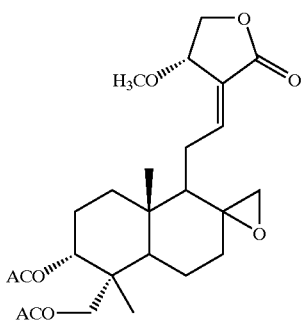

Step 1

14-METHOXY 8,17-EPOXY ANDROGRAPHOLIDE 3,19-ACETONIDE 8,17-epoxy andrographolide 3,19-acetonide (500 mg) was treated with calcium sulphate (550 mg) in 5 ml of methyl iodide. The mixture was treated with silver oxide (465 mg) and the contents were stirred at room temperature for 28 hours. The reaction was monitored by TLC. After completion of the reaction, the reaction mixture was extracted with dichloromethane and filtered through celite. The filtrate was concentrated, chromatographed over a column of silica gel (60–120) with chloroform: acetone mixture (96:4) to yield 14-methoxy 8,17-epoxy andrographolide 3,19-acetonide (350 mg, 67%).

Step 2

14-METHOXY 8,17-EPOXY ANDROGRAPHOLIDE 14-methoxy 8,17-epoxyandrographolide 3,19-acetonide (350 mg) obtained in step 1 above was stirred with 100 ml of 70% aqueous acetic acid for 10 min. After completion of the reaction the reaction mixture was neutralized with sodium bicarbonate and extracted with dichloromethane. The organic layer was dried with sodium sulphate and concentrated to yield crude 14-methoxy 8,17-epoxy andrographolide (300 mg, 95%).

Step 3

14-METHOXY 3,19-DIACETYL 8,17-EPOXY ANDROGRAPHOLIDE

14-Methoxy 8,17-epoxy andrographolide (300 mg) obtained above was refluxed in acetic anhydride (10 ml) for about 10 min. After completion of the reaction the reaction mixture was poured into water and extracted with dichloromethane. The residue obtained after removing the solvent was purified by flash chromatography over a column of silica gel (230–400 mesh) with pet. ether:ethyl acetate (65:35) to yield 14-methoxy 3,19-diacetyl 8,17-epoxy andrographolide (260 mg, 71%). m.p. 164° C.

¹H NMR: δ7.1 (1H, t, C=12), 4.7–4.6 (m), 4.4 & 4.15 (2H, dd, C-19), 4.35 (2H, d, C-15), 3.3 (3H, s, —OMe), 2.65 (2H, dd, C-17), 2.10, 2.15 (3H each, s, OAc).

EXAMPLE 7

PREPARATION OF 14-CINNAMOYL 3,19-DIHYDROXY 8,17-EPOXY ANDROGRAPHOLIDE

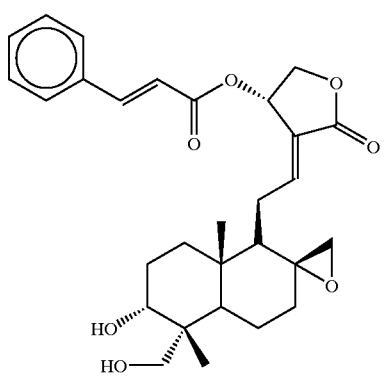

Step 1

14-CINNAMOYL 8,17-EPOXY ANDROGRAPHOLIDE 3,19-ACETONIDE

Mixed anhydride of cinnamic acid and ethyl chloro formate was prepared by adding 270 μl of ethyl chloro formate and 500 μl of triethyl amine in succession to a solution of cinnamic acid (370 mg) in 25 ml of dichloromethane at 0° C. under nitrogen atmosphere. The mixture was stirred for 30 minutes at 0° C. To this 500 mg of 8,17-epoxy andrographolide 3,19-acetonide in dichloromethane was added dropwise. The resultant mixture was stirred at room temperature for about 12 hours. The reaction was monitored by TLC. After completion of the reaction, the reaction mixture was diluted with dichloromethane, washed with saturated $NaHCO_3$ followed by water and dried over $Na_2SO_4$ and concentrated. The residue was chromatographed over a column of silica gel (230–400 mesh) using chloroform:acetone (98:2) as the eluting solvent.

Step 2

14-CINNAMOYL 8,17-EPOXY ANDROGRAPHOLIDE

14-Cinnamoyl ester of 8,17-epoxy andrographolide 3,19-acetonide obtained above (300 mg) was treated with 70% aq. acetic acid to yield the title compound as a colourless solid (250 mg) m.p. 97° C.

$^1$H NMR: δ7.7 (1H, d, J=20 Hz, C-3'), 7.5 (2H, m), 7.35(3H, m), 7.05 (1H, triplet, C-12), 6.4(1H, d, J=20 Hz, C-2'), 6.0 (1H, d, J=5.8 Hz, C-14), 4.6–4.5 (m), 4.3–4.1 (m), 3.4 (m, C-3), 3.3 (d, C-19 Hb), 2.5 (2H, dd, C-17H).

EXAMPLE 8

PREPARATION OF 14-CINNAMOYL 3,19-DIPROPIONYL 8,17-EPOXY ANDROGRAPHOLIDE

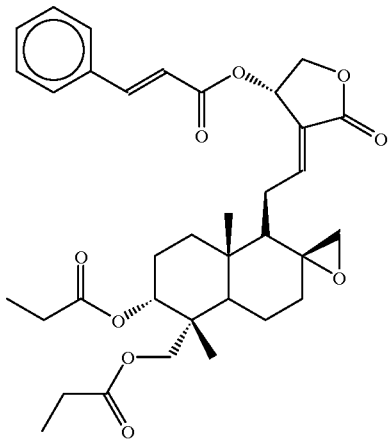

250 mg of the 14-cinnamoyl 8,17-epoxy andrographolide obtained in Example 7 was refluxed in 10 ml of propionic anhydride for 15 minutes. The reaction was monitored by TLC. After completion of the reaction, the reaction mixture was poured into water and extracted with dichloromethane. The dichloromethane layer was dried over sodium sulfate and concentrated. The residue was chromatographed over a column of silicagel with light petrol:acetone (9:1) as the eluting system to obtain the title compound as a colourless solid (100 mg, 32%) m.p. 108° C.

$^1$H NMR: δ7.7 (1H, d, J=20 Hz, C=3'H), 7.5 (2H, m), 7.45 (3H, m), 7.1 (1H, t, J=10 Hz, C-12H), 6.4 (1H, d, J=20 Hz, C=2'H), 6.0 (1H, d, J=5.8 Hz, C-14 H), 4.6–4.5 (m), 4.4–4.0 (m), (m, C-3H), 2.5 (2H, dd, C-17 H), 2.35–2.20 (propionyl)

EXAMPLE 9

PREPARATION OF 14-[4'-METHOXYCINNAMOYL]3,19-DIPROPIONYL 8, 17-EPOXY ANDROGRAPHOLIDE

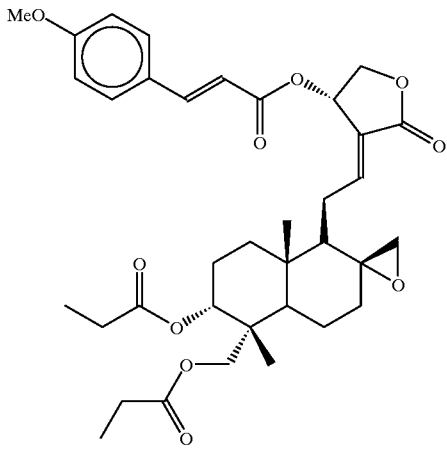

Step 1

14-[4-METHOXYCINNAMOYL]8,17-EPOXY ANDROGRAPHOLIDE 3,19-ACETONIDE

Mixed anhydride of 4-methoxy cinnamic acid and ethyl chloro formate was prepared by adding 150 μl of ethyl chloro formate and 250 μl of triethyl amine in succession to a solution of 4-methoxycinnamic acid (250 mg) in 25 ml of dichloromethane at 0° C. under nitrogen atmosphere. The mixture was stirred for 30 minutes at 0° C. To this reaction mixture, a solution of 200 mg of 8,17-epoxy andrographolide 3,19-acetonide in dichloromethane was added dropwise. The resultant mixture was stirred at room temperature for about 12 hours. The reaction was monitored by TLC. After completion of the reaction, the reaction mixture was diluted with dichloromethane, washed with saturated $NaHCO_3$ followed by water and dried over $Na_2SO_4$ and concentrated. The residue was chromatographed over a column of silica gel (230–400 mesh) using chloroform:acetone (98:2) as the eluting solvent to obtain the title compound in 89% yield.

Step 2

14-[4-METHOXYCINNAMOYL]8,17-EPOXY ANDROGRAPHOLIDE

The 14-[4-methoxycinnamoyl]ester of 8,17-epoxy andrographolide 3,19-acetonide obtained above (120 mg) was treated with 70% aq. acetic acid to get 110 mg of the 14-[4-methoxycinnamoyl]8,17-epoxy andrographolide in quantitative yield.

Step 3

8,17-EPOXY 14-[4-METHOXYCINNAMOYL]3, 19-DIPROPIONYL ANDROGRAPHOLIDE 110 mg of the 14-[4-methoxycinnamoyl]8,17-epoxy andrographolide obtained above was refluxed in 10 ml of propionic anhydride for 15 minutes. The reaction was monitored by TLC. After completion of the reaction, the reaction mixture was poured into water and extracted with dichloromethane. The dichloromethane layer was dried and concentrated. The residue was chromatographed over a column of silicagel with light petrol:acetone (9:1) as the eluting system to obtain the title compound as a colourless solid (80 mg, 60%) m.p. 111.8° C.

$^1$H NMR: δ7.7 (1H, d, J=20 Hz, C-3'H), 7.5 (2H, d, J=10 Hz,) 7.15 (1H, t, J=10 Hz, C-12H), 6.95 (2H, d, J=10 Hz), 6.30 (1H, d, J=20 Hz, C-2'), 6.0 (1H, d, C-14), 4.7–4.5 (m), 4.4–4.0 (m), 3.85 (3H, s) 2.55 (2H, dd, C-17), 2.4–22. (m, Propyl).

EXAMPLE 10

PREPARATION OF 8,17-EPOXY 14-[3',4'-DIMETHOXYCINNAMOYL]3,19-DIPROPIONYL ANDROGRAPHOLIDE

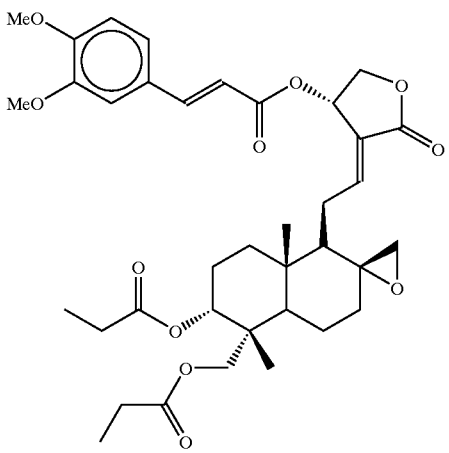

Step 1

14-[3'4'-DIMETHOXYCINNAMOYL]8,17-EPOXY ANDROGRAPHOLIDE 3,19-ACETONIDE

Mixed anhydride of 3,4-dimethoxy cinnamic acid and ethyl chloro formate was prepared by adding 150 μl of ethyl chloro formate and 250 μl of triethyl amine in succession to a solution of 3,4-dimethoxycinnamic acid (250 mg) in 25 ml of dichloromethane at 0° C. under nitrogen atmosphere. The mixture was stirred for 30 minutes at 0° C. To this reaction mixture 200 mg of 8,17-epoxy andrographolide 3,19-acetonide in dichloromethane was added dropwise. The resultant mixture was stirred at room temperature for about 12 hours. The reaction mixture was monitored by TLC. After completion of the reaction, the reaction mixture was diluted with dichloromethane, washed with saturated $NaHCO_3$ followed by water and dried over $Na_2SO_4$ and concentrated. The residue was chromatographed over a column of silica gel (230–400 mesh) using chloroform:acetone (98:2) as the eluting solvent to obtain the title compound in 44% yield.

Step 2

14-[3,4-DIMETHOXYCINNAMOYL]8,17-EPOXY ANDROGRAPHOLIDE

The 14-[3',4'-dimethoxycinnamoyl]ester of 8,17-epoxy andrographolide 3,19-acetonide obtained in the step 1 (120 mg) was treated with 70% aq. acetic acid to get 110 mg of the 14-[3,4-dimethoxycinnamoyl]8,17-epoxy andrographolide quantitatively.

Step 3

14-[3',4'-DIMETHOXYCINNAMOYL]3,19-DIPROPIONYL 8,17-EPOXY ANDROGRAPHOLIDE 110 mg of the 14-[3,4-dimethoxycinnamoyl]8,17-epoxy andrographolide was refluxed in 10 ml of propionic anhydride for 15 minutes. The reaction was monitored by TLC. After completion of the reaction, the reaction mixture was poured into water and extracted with dichloromethane. The dichloromethane layer was dried and concentrated. The residue was chromatographed over a column of silicagel with light petrol:acetone (9:1) as the eluting system to yield the title compound as a colourless solid (80 mg, 60%) m.p 128.8° C.

$^1$H NMR: δ7.7 (1H, d, J=20 Hz, C-3'H), 7.2–7.05 (3H, m, C-6',9' & 12), 6.9 (1H, d, J=10 Hz, C-5'), 6.45 (1H, d, J=20 Hz, C-2'), 6.0 (1H, d, J=5.8 Hz, C-14), 4.7–4.5 (m), 4.4–4.0 (m), 3.9 (6H, s) 2.6 (1H, d, C-17), 2.4–2.2 (m, Propyl).

EXAMPLE 11

PREPARATION OF 14-[3',4'-METHYLENEDIOXYCINNAMOYL]3,19-DIPROPIONYL 8,17-EPOXY ANDROGRAPHOLIDE

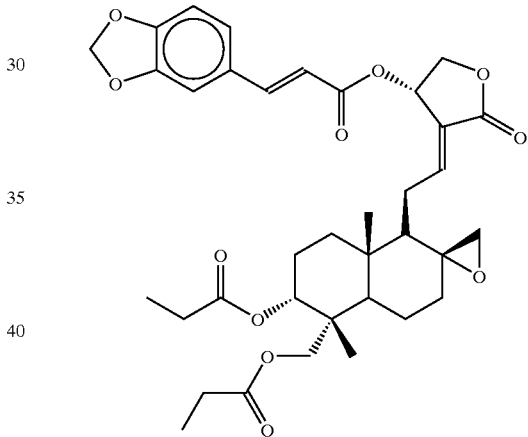

Step 1

14-[3',4'-METHYLENEDIOXY]8,17-EPOXY ANDROGRAPHOLIDE 3,19-ACETONIDE

The mixed anhydride of 3,4-methylenedioxycinnamic acid and ethyl chloro formate was prepared by adding 270 μl of ethyl chloro formate and 500 μl of triethyl amine in succession to a solution of 3,4-methylenedioxy cinnamic acid (475 mg) in 25 ml of dichloromethane at 0° C. under nitrogen atmosphere. The mixture was stirred for 30 minutes at 0° C. To this 400 mg of 8,17-epoxy andrographolide 3,19-acetonide in dichloromethane was added dropwise. The resultant mixture was stirred at room temperature for about 12 hours. The reaction was monitored by TLC. After completion of the reaction, the reaction mixture was diluted with dichloromethane, washed with saturated $NaHCO_3$ followed by water and dried over $Na_2SO_4$ and concentrated. The residue was chromatographed over a column of silica gel (230–400 mesh) using chloroform:acetone (98:2) as the eluting solvent to yield 53% of 14-[3',4'-methylenedioxy]8,17-epoxy andrographolide 3,19-acetonide.

Step 2

14-[3',4'-METHYLENEDIOXY]8,17-EPOXY ANDROGRAPHOLIDE

The 14-[3',4'-methylenedioxy cinnamoyl]ester of 8,17-epoxy andrographolide 3,19-acetonide obtained in step 1 above (300 mg) was treated with 70% aq. acetic acid to get 200 mg (71% yield) of the 14-[3',4'-methylenedioxy cinnamoyl]8,17-epoxy andrographolide.

Step 3

14-[3',4'-METHYLENEDIOXY CINNAMOYL]3, 19-DIPROPIONYL 8,17-EPOXY ANDROGRAPHOLIDE 200 mg of the 14-[3',4'-methylenedioxy cinnamoyl]8,17-epoxy andrographolide obtained in step 2 above was refluxed in 10 ml of propionic anhydride for 15 minutes. The reaction was monitored by TLC. After completion of the reaction, the reaction mixture was poured into water and extracted with dichloromethane. The dichloromethane layer was dried and concentrated. The residue was chromatographed over a column of silicagel with light petrol:acetone (9:1) as the eluting system to yield 14-[3',4'-methylenedioxy cinnamoyl]3,19-dipropionyl 8,17-epoxyandrographolide as colourless solid (180 mg, 75%) m.p. 76.7° C.

$^1$HNMR: 7.65 (1H, d, J=20 Hz, C-3'), 7.15 (1H, t, J=10 Hz, C-12), 7.0 (2H, m C-5' & 9'), 6.8 (1H, d, C-6'), 6.25 (1H, d, J=20 Hz, C-2'), 6.0 (3H, m, C-14 & C-10') 4.7–4.5 (m), 4.4–4.0 (m), 2.55 (1H,d, C-17), 2.4–2.2 (m, Propyl).

EXAMPLE 12

PREPARATION OF 14-[N-BOC GLYCINY]8,17-EPOXY ANDROGRAPHOLIDE

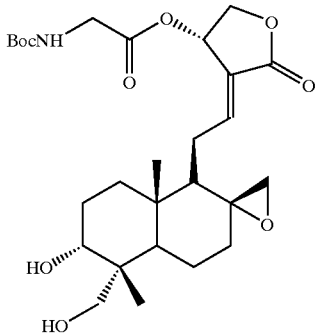

Step 1

14-[N-BOC GLYCINYL]8,17-EPOXY ANDROGRAPHOLIDE 3,19-ACETONIDE

14-[N-Boc glycinyl]8,17-epoxy andrographolide 3,19-acetonide was prepared by treating 8,17-epoxy andrographolide 3,19-acetonide with the mixed anhydride of N-Boc glycine and ethyl chloro formate. The mixed anhydride of N-Boc glycine and ethyl chloro formate was prepared by adding 1.75 ml of ethyl chloro formate and 2 ml of triethyl amine in succession to a solution of N-Boc glycine (2 gms) in 25 ml of dichloromethane at −40° C. under nitrogen atmosphere. The mixture was stirred for 15 minutes at −40° C. To this 1 gram of 8,17-epoxy andrographolide 3,19-acetonide in 10 ml dichloromethane and 0.5 ml triethyl amine were added. The resultant mixture was stirred at room temperature for about 3 hours. The reaction was monitored by TLC. After completion of the reaction, the reaction mixture was diluted with dichloromethane, washed with saturated $NaHCO_3$ followed by water and dried over $Na_2SO_4$ and concentrated to yield 14-[N-Boc glycinyl]8,17-epoxy andrographolide 3,19-acetonide.

Step 2

14-[N-BOC GLYCINYL]8,17-EPOXY ANDROGRAPHOLIDE

14-[N-Boc glycinyl]8,17-epoxy andrographolide 3,19-acetonide obtained above was treated with 70% aq. acetic acid to yield 600 mg of the 14-[N-Boc glycinyl]ester of 8,17-epoxy andrographolide. The residue was chromatographed over a column of silica gel (230–400 mesh) using chloroform:acetone (9:1) to yield 48% of the pure compound. m.p. 98° C.

$^1$H NMR: δ7.1 (1H, t, J=10 Hz, C-12), 6.00 (1H, d, J=5.8 Hz, C-14), 5.05 (1H, broad singlet NH), 4.7–4.5 (m), 4.35–4.15 (m), 3.95 (2H), 3.55 (1H, m, C-3H), 3.35 (1H, d, C-19), 2.6 (1H,dd, J=12, 4 Hz, C-17 H).

EXAMPLE 13

PREPARATION OF 14-[N-BOC GLYCINYL]3,19-DIPROPIONYL 8,17-EPOXY ANDROGRAPHOLIDE

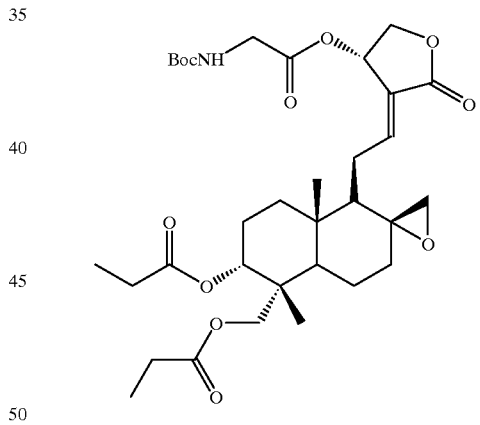

300 mg of the 14-[N-Boc glycinyl]8,17-epoxy andrographolide obtained in Example 12 was refluxed in 10 ml of propionic anhydride at 180° C. for 5 minutes. The reaction was monitored by TLC. After completion of the reaction, the reaction mixture was poured into water and extracted with dichloromethane. The dichloromethane layer was dried and concentrated. The residue was chromatographed over a column of silicagel with chloroform:acetone (98:2) as the eluting system to yield the title compound as a colourless solid (160 mg, 44%) m.p 86° C.

$^1$H NMR: δ7.05 (1H, t, J=10 Hz, C-12), 5.95 (1H, d, J=5.8 Hz, C-14), 5.00 (1H, broad singlet NH), 4.7–4.4 (m), 4.35–4.00 (m), 3.85 (2H), 2.55 (1H,dd, J=12, 4 Hz, C-17 H), 2.35–2.20 (propionyl)

EXAMPLE 14

PREPARATION OF 19-TRITYL 8,17-EPOXY ANDROGRAPHOLIDE

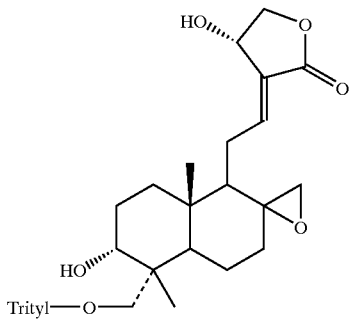

Step 1
19-TRITYL ANDROGRAPHOLIDE

A mixture of andrographolide (5 gms) and trityl chloride (10 gms) in dry pyridine were heated to 80° C. under Nitrogen atmosphere. The heating was continued for 4 hours and the mixture was left at room temperature overnight. The mixture was diluted with solvent ether and washed with water. The organic layer was dried and freed from the solvent. The residue was chromatographed over a column of silicagel with chloroform:acetone (95:5) as the eluent system to obtain 6 gms of 19-trityl andrographolide.

Step 2
19-TRITYL 8,17 EPOXY ANDROGRAPHOLIDE 19-trityl andrographolide (4 gms) obtained in the step 1 was taken in 100 ml of DCM and treated with m-chloro perbenzoic acid. The reaction mixture was stirred at room temperature for 8 hours, concentrated and purified by flash chromatography over a column of silicagel with chloroform:acetone (95:5) to get 19-trityl 8,17 epoxy andrographolide (3.5 gins) m.p: 128° C.

$^1$H NMR: δ7.5–7.15 (15H, m, Aromatic CH), 6.75 (1H, t, C-13A), 4.95 (1H, d, J=4.8 Hz, C-14H), 4.4–4.1 (m), 3.4–3.1 (m), 2.65 (2H, dd, J=12.4 Hz, C-17H).

EXAMPLE 15

PREPARATION OF 3-ACETYL 8,17-EPOXY ANDROGRAPHOLIDE

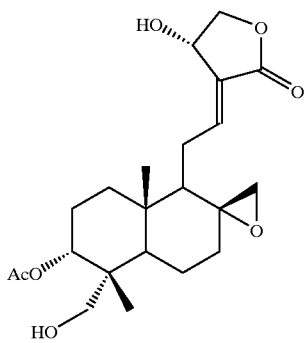

Step 1
3-ACETYL 19-TRITYL 8,17-EPOXY ANDROGRAPHOLIDE & 3,14-DIACETYL 19-TRITYL 8,17-EPOXY ANDROGRAPHOLIDE 19-trityl 8,17-epoxy andrographolide (500 mg) obtained in Example 14 was heated in acetic anhydride (15 ml) for 10 minutes at 140° C. The reaction was monitored by TLC. After completion of the reaction, the mixture was poured into cold water and extracted with dichloromethane. The dichloromethane layer was dried over $Na_2SO_4$ and freed from the solvent. The residue was shown to contain two compounds. The residue was chromatographed over a column of silica gel (60–120) with chloroform:acetone (99:1) as the eluting system to yield 3-acetyl 19-trityl 8,17-epoxy andrographolide (150 mg) and 3,14-diacetyl 19-trityl 8,17-epoxy andrographolide (165 mg).

Step 2
3-ACETYL 8,17-EPOXY ANDROGRAPHOLIDE

3-Acetyl 19-trityl 8,17-epoxy Andrographolide (100 mg) obtained above was taken in 10 ml of dichloromethane and 5 ml of formic acid was added to the solution. The mixture was stirred for 15 minutes. The mixture was neutralized by passing ammonia and the precipitate of ammonium formate obtained was filtered. The dichloromethane layer was washed with water, dried over $Na_2SO_4$ and freed from the solvent. The residue obtained was purified by chromatography over a column of silicagel (60–120) with chloroform:acetone (85:15) to yield the title compound as a colourless solid(50 mg) m.p: 194.3° C.

$^1$H NMR: 6.8 (1H, t, J=10 Hz, C-12 H), 5.0 (1H, d, J=5.5 Hz, C-14 H), 4.75–4.5 (m)), 4.4–4.0 (m), 3.45 (1H, d, C-19 Hb), 2.8 (2H, dd, J=12, 4 Hz C-17H)

EXAMPLE 16

PREPARATION OF 3,14-DIACETYL 8,17-EPOXY ANDROGRAPHOLIDE

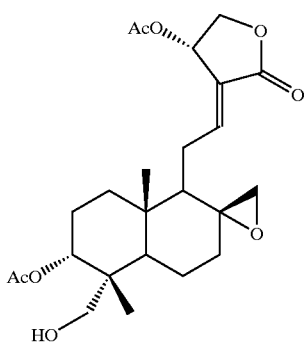

Step 1
ACETYL DERIVATIVE OF 19-TRITYL 8,17-EPOXY ANDROGRAPHOLIDE 19-trityl 8,17-epoxy andrographolide (500 mg) obtained in Example 14 was heated in acetic anhydride (15 ml) for 10 minutes at 140° C. The reaction was monitored by TLC. After completion of the reaction the mixture was poured into cold water and extracted with dichloromethane. The dichloromethane layer was dried over $Na_2SO_4$ and freed from the solvent. The residue was chromatographed over a column of silica gel (60–120) with chloroform:acetone (99:1) as the eluting system to yield 3-acetyl 19-trityl 8,17-epoxy andrographolide (150 mg) and 3,14-diacetyl 19-trityl 8,17-epoxy andrographolide (165 mg).

Step 2
3,14-DIACETYL 8,17-EPOXY ANDROGRAPHOLIDE 3,14-diacetyl 19-trityl 8,17-epoxy andrographolide (100 mg) obtained above was taken in 10 ml of dichloromethane and 5 ml of formic acid was added to the solution. The mixture was stirred for 15 minutes. After completion of the reaction, the mixture was diluted with solvent ether, washed with saturated NaHCO₃ solution and water. The ether layer was dried over sodium sulfate and freed from solvent. The residue was chromatographed over a column of silica gel (60–120) with chloroform:acetone (90:10) to yield the title compound as a colourless solid (50 mg) m.p.: 167.9° C.

¹H NMR: 7.1 (1H, t, J=10 Hz, C-12 H), 5.9 (1H, d, J=5.5 Hz, C-14 H), 4.75–4.40 (m,), 4.3–4.0 (m), 3.40 (1H, d, C-19 Hb), 2.6 (2H, dd, J=12, 4 Hz, C-17H), 2.15(3H, s, Acetyl), 2.10 (3H, s, Acetyl).

EXAMPLE 17

PREPARATION OF 14,19-DIACETYL 8,17-EPOXY ANDROGRAPHOLIDE

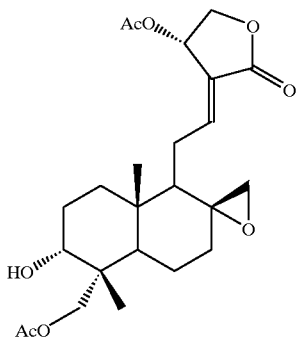

800 mg of 8,17-epoxy andrographolide obtained in Example 1 was dissolved in a mixture of acetic anhydride (10 ml) and pyridine (520 μl) at −7° C. and stirred for 2 hrs under nitrogen atmosphere. After completion of the reaction it was taken in 50 ml of dichloromethane and washed with saturated copper sulphate solution followed by water. The organic layer was dried over sodium sulphate and freed from the solvent. The residue was chromatographed over a column of silica gel and eluted with light petrol:acetone mixture (80:20 to 75:25) to yield the title compound as colourless solid (200 mg, 20%) m.p: 135.4° C.

¹H NMR: δ7.1 (1H, t, J=10 Hz, C-12 H), 5.85 (1H, d, J=5.8 Hz, C-14 H), 4.6–4.4(m,), 4.4–4.0(m), 3.5–3.2 (1H, m, C-3H) 2.55 (2H, dd, J=12, 4 Hz, C-17H), 2.25(3H, s, acetyl) 2.15 (3H, s, acetyl).

EXAMPLE 18

PREPARATION OF 3,14-DIPROPIONYL 8,17-SPIROEPOXY ANDROGRAPHOLIDE

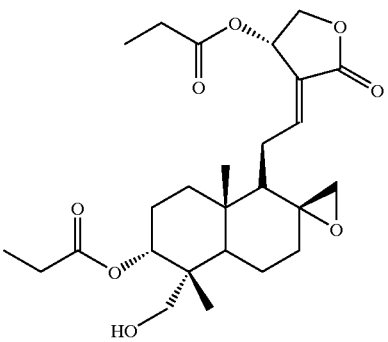

Step 1

3,14-DIPROPIONYL 19-TRITYL 8,17-EPOXY ANDROGRAPHOLIDE 19-trityl 8,17-epoxy andrographolide (1 gram) obtained in example 14 was refluxed in propionic anhydride (20 ml) at 180° C. for 5 minutes. After completion of the reaction, the reaction mixture was cooled, diluted with water and extracted with dichloromethane. The organic layer was washed with water, dried over Na₂SO₄ and freed from the solvent. The residue obtained was chromatographed over a column of silicagel with chloroform:acetone (98:2) to yield 3,14-dipropionyl 19-trityl 8,17-epoxy andrographolide.

Step 2

3,14-DIPROPIONYL 8,17-EPOXY ANDROGRAPHOLIDE 3,14-dipropionyl 19-trityl 8,17-epoxy andrographolide obtained above was dissolved in 50% formic acid in dichloromethane and stirred at room temperature for 10 minutes. The mixture was diluted with solvent ether, washed with bicarbonate and water successively. The organic layer was dried over Na₂SO₄ and the residue obtained after removal of the solvent was chromatographed over a column of silicagel with chloroform:acetone (9:1) to yield the title compound as a colourless solid (200 mg). m.p.: low melting solid.

¹H NMR: 7.1 (1H, t, J=10 Hz, C-12 H), 5.9(1 H, d, J=5.5 Hz, C-14 H), 4.75 (1H, m, 15Ha), 4.4–4.0 (m), 3.45 (1H, d, C-19 Hb), 2.6 (2H, dd, J=C-17H), 2.35 (6H, m, propionyl)

Anti-cancer activity

The compounds prepared in the present invention exhibited good in vitro anti-cancer activity towards various human tumor cell lines.

Each test compound was screened against a battery of cell lines representing eight different types of cancer. In a typical procedure 1×10⁴ cells were seeded into each well of 96-well plates in 100 μL volume of RPMI-1640 containing antibiotics and 10% FCS.

The plates were incubated at 37° C. in presence of CO₂. After 24 h, test compounds were evaluated at five 10 fold dilutions ranging from 100 to 0.01 μM. To each test well 100 μL of test compound solution was added and medium with vehicle was added to control wells and the plates were further incubated. After 48 h of incubation, plates were terminated by Sulforhodamine B method.

The optical density which is proportional to protein mass, is then read by automated spectrophotometric plate readers at a wavelength of 515 nm. Readings were transferred to a microcomputer and mean 50% Growth Inhibition (GI50) and mean Total Growth Inhibition were observed. The compounds of the present invention showed anticancer activity as can be seen from the data given below:

| PANEL/CELL LINES | GROWTH INHIBITION (GI 50) [μm] | | | | | |
|---|---|---|---|---|---|---|
| | Example-2 | Example-4 | Example-7 | Example-8 | Example-9 | Example-10 |
| BREAST: | | | | | | |
| MCF-7/ADR | 5.5 | 0.8 | 2.0 | 0.08 | 3.0 | 1.5 |
| CNS: | | | | | | |
| U251 | 3.0 | 0.8 | 6.0 | 6.0 | 3.0 | 2.0 |
| COLON: | | | | | | |
| SW-620 | 1.0 | 25.0 | 0.5 | 2.5 | 0.6 | 0.4 |
| LUNG: | | | | | | |
| H522 | 20.0 | 5.5 | 6.0 | 20.0 | 4.8 | 7.5 |
| MELANOMA: | | | | | | |
| UACC62 | | 0.55 | | | | |
| M14 | 7.5 | | 1.0 | 2.5 | 0.75 | 0.8 |
| OVARIAN | | | | | | |
| SKOV-3 | 4.0 | 0.45 | 4.0 | 10.0 | 2.0 | 2.5 |
| PROSTATE: | | | | | | |
| DU145 | 20 | 4.5 | 5.5 | 4.0 | 2.0 | 2.5 |
| RENAL | | | | | | |
| A498 | 0.1 | 15.0 | 9.0 | 3.0 | 3.0 | 3.5 |

| PANEL/CELL LINES | TOTAL GROWTH INHIBITION (TGI) [μm] | | | | | |
|---|---|---|---|---|---|---|
| | Example-2 | Example-4 | Example-7 | Example-8 | Example-9 | Example-10 |
| BREAST: | | | | | | |
| MCF-7/ADR | 40.0 | 5.0 | 6.0 | 4.0 | 7.5 | 6.5 |
| CNS: | | | | | | |
| U251 | 8.0 | 10.0 | 20.0 | 20.0 | 6.0 | 5.5 |
| COLON: | | | | | | |
| SW-620 | 7.0 | 70.0 | 1.5 | 5.0 | 2.0 | 0.75 |
| LUNG: | | | | | | |
| H522 | 70.0 | 50.0 | 30.0 | 60.0 | 15.0 | 40.0 |
| MELANOMA: | | | | | | |
| UACC62 | | 8.0 | | | | |
| M14 | 70.0 | | 4.5 | 7.5 | 3.0 | 9.0 |
| OVARIAN | | | | | | |
| SKOV-3 | 7.0 | 7.5 | 8.0 | 40.0 | 5.0 | 5.2 |
| PROSTATE: | | | | | | |
| DU145 | 60.0 | 15.0 | 20.0 | 10.0 | 5.5 | 6.2 |
| RENAL | | | | | | |
| A498 | 7.0 | 75.0 | 90.0 | 7.0 | 7.0 | >100 |

Metabolic Disorders (a) Efficacy in genetic models

Mutation in colonies of laboratory animals and different sensitivities to dietary regimens have made the development of animal models with non-insulin dependent diabetes and hyperlipidemia associated with obesity and insulin resistance possible. Genetic models such as db/db mice have been developed by the various laboratories for understanding the pathophysiology of disease and testing the efficacy of new antidiabetic compounds (Diabetes, (1983) 32: 830–838; Annu. Rep. Sankyo Res. Lab. (1994). 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

Male C57BL/KsJ-db/db mice of 8 to 14 weeks age, having body weight range of 35 to 60 grams, bred at Dr. Reddy's Research Foundation (DRF) animal house, were used in the experiment. The mice were provided with standard feed (National Institute of Nutrition (NIN), Hyderabad, India) and acidified water, ad libitum. The animals having more than 350 mg/dl blood sugar were used for testing. The number of animals in each group was 4.

Test compounds were suspended in chemophore/DMSO/H$_2$O and administered to test group at a dose of 0.1 to 500 mg/kg through oral gavage daily for 6 days. The control group received vehicle (dose 10 ml/kg). On 6th day the blood samples were collected one hour after administration of test compounds/vehicle for assessing the biological activity.

The random blood sugar and triglyceride levels were measured by collecting blood (100 µl) through orbital sinus, using heparinised capillary in tubes containing EDTA which was centrifuged to obtain plasma. The plasma glucose and triglyceride levels were measured spectrometrically, by glucose oxidase and glycerol-3-PO$_4$ oxidase/peroxidase enzyme (Dr. Reddy's Lab. Diagnostic Division Kits, Hyderabad, India) methods respectively.

The blood sugar and triglycerides lowering activities of the test compound was calculated according to the formula.

Formulae for calculation:

1. Percent reduction in Blood Sugar/triglycerides were calculated according to the formula:

$$\text{Percent reduction (\%)} = \left[1 - \frac{TT/OT}{TC/OC}\right] \times 100$$

OC=Zero day control group value
OT=Zero day treated group value
TC=Test day control group value
TT=Test day treated group value Body weight of the animals were measured at the beginning and at the end of the study period.

No adverse effects were observed for any of the mentioned compounds of invention in the above test.

The experimental results from the db/db mice, suggest that the novel compounds of the present invention also possess therapeutic utility as a prophylactic or regular treatment for diabetes, obesity, cardiovascular disorders such as hypertension, hyperlipidaemia and other diseases; as it is known from the literature that such diseases are interrelated to each other.

(b) Plasma triglyceride and body weight reduction in Swiss albino mice Male Swiss albino mice (SAM) were obtained from NIN and housed in DRF animal house. All these animals were maintained under 12 hour light and dark cycle at 25±1° C. Animals were given standard laboratory chow (NIN, Hyderabad, India) and water, ad libitum. SAM of 20–25 g body weight range (Oliver, P., Plancke, M. O., Marzin, D., Clavey, V., Sauzieres, J and Fruchart, J. C. Effects of fenofibrate, gemfibrozil and nicotinic acid on plasma lipoprotein levels in normal and hyperlipidemic mice. Atherosclerosis. 1988. 70: 107–114).

The test compounds were administered orally to Swiss albino mice at 0.3 to 500 mg/kg dose for 6 days. Control mice were treated with vehicle (Chremophore/DMSO/H$_2$O; dose 10 ml/kg).

The blood samples were collected in fed state 1 hour after drug administration on 0 and 6 day of treatment. The blood was collected from the retro-orbital sinus through heparinised capillary in EDTA containing tubes. After centrifugation, plasma sample was separated for triglyceride (Wieland, O. Methods of Enzymatic analysis. Bergermeyer, H. O., Ed., 1963. 211–214; Trinder, P. Ann. Clin. Biochem. 1969. 6: 24–27). Measurement of plasma triglyceride was done using commercial kits (Dr. Reddy's Diagnostic Division, Hyderabad, India).

| Example | Dose (mg/kg) | Percentage reduction TG | Body weight |
|---|---|---|---|
| Example-2 | 250 mg/kg | 19 | — |
| Example-7 | 250 mg/kg | 52 | 13% |
|  | 100 mg/kg | 42 | 29% |
|  | 500 mg/kg | 62 | — |
| Example-13 | 250 mg/kg | 31 | — |

The formula used to measure percent reduction in blood sugar/triglycerides is given above.

Anti HIV Activity

Human CD4+ T cell line PM-1 used in the assay was cultured in RPMI-1640 medium containing 10% Fetal bovine serum, 2 g/L sodium bicarbonate, 100,000 units/L Pencillin-G and 100 mg/L streptomycin. Healthy PM-1 cells were plated on the first day in a 96 well plate at 2×10$^6$ cells per well. After 24 h HIV-1/MN was added to the culture and incubated for 2 h for infection. Cells were washed twice with PBS to remove the virus in the culture. Different concentrations of DRF compounds ranging from 10$^{-4}$ to 10$^{-8}$ M were added to the culture and incubated for 96 h. The viability of cells was then assessed by standard MTT assay and the viral antigen P24 levels were estimated by ELSA method. Based on the MTT assay values the P 24 antigen values were corrected.

All the samples were tested in triplicates and the average was used for calculations. AZT was used as standard compound for comparison.

| Example | Concentration | Percent Inhibition |
|---|---|---|
| Example-2 | 1 µM | 77.25 |
|  | 0.1 µM | 75.31 |
| Example-7 | 1 µM | 68.37 |
| Example-13 | 1 µM | 73.94 |

Lymphocyte Proliferation

Human lymphocycles were isolated from whole blood by using Ficoll Hypaque Plus (Amersham). On day one, 1 million lymphocytes were seeded into each well of 96 well plate in 100 µL volume of RPMI 1640 medium containing 10% FCS and Phytohemagglutitin A at 10 µg/ml concentration. Plates were incubated at 37° C. in $CO_2$ incubator for 24 h. Test compounds at various concentrations were added to test wells and only medium with vehicle was added to control wells. After 48 h of incubation 0.5 mCi of tritiated thymidine was added to each well. After 24 h of thymidine addition the cells were harvested and the incorporated radioactivity was determined.

Stimulation index (si) was calculated using the formula, $$SI = \frac{A^T - A^C}{A^C} \times 100$$

$A^T$ = Average CPM of treated wells,
$A^C$ = Average CPM of control wells.

| Example | Concentration | Stimulation Index (SI) |
|---|---|---|
| Example-2 | 1 µM | 32 |
| Example-7 | 1 µM | 25 |
| Example-13 | 1 µM | 24 |

What is claimed is:

1. A compound of formula (I)

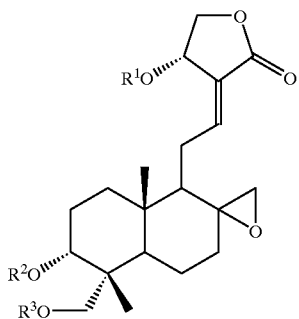

I where $R^1$, $R^2$ and $R^3$ are the same or different and independently represent hydrogen or substituted or unsubstituted groups selected from alkyl, aryl, heteroaryl, aralkyl, heteroaralkyl, alkanoyl, alkenoyl, aroyl, heteroaroyl, sulfonyl group or a group —(CO)—W—$R^4$ where W represents O, S, or $NR^5$, wherein $R^5$ represents hydrogen or ($C_1$–$C_6$) alkyl group, $R^4$ represents substituted or unsubstituted groups selected from alkyl, aryl, aroyl, or aralkyl or $R^2$ and $R^3$ together form a substituted or unsubstituted 3 to 7 membered cyclic structure containing carbon and oxygen atoms; its stereoisomers, its polymorphs, its salts and its solvates.

2. The compound according to claim 1, wherein the substituents on $R^1$, $R^2$ and $R^3$ are selected from cyano, hydroxy, nitro, halogen atom or substituted or unsubstituted groups selected from ($C_1$–$C_8$)alkyl, amino, mono or disubstituted amino, alkanoyl, ($C_1$–$C_6$) alkoxy, aroyl, acyloxy, aryl, heteroaryl, mono($C_1$–$C_6$) alkylamino, di($C_1$–$C_6$) alkylamino, acylamino, arylamino, aralkylamino, alkoxycarbonylamino, aryloxycarbonylamino, aralkoxycarbonylamino, or COOR, where R represents hydrogen or ($C_1$–$C_6$)alkyl group.

3. The compound according to claim 2, wherein when the alkyl group is substituted, the substituents are selected from halogen, hydroxy, nitro, cyano, amino, phenyl or ($C_1$–$C_6$) alkoxy.

4. The compound according to claim 2, wherein when the amino group is substituted the substituents are selected from hydroxy or ($C_1$–$C_6$)alkoxy.

5. The compound according to claim 2, wherein the aryl group is mono or disubstituted the substituents are selected from ($C_1$–$C_6$)alkyl, halogen atom, amino, cyano, hydroxy, nitro, trifluoroethyl, or ($C_1$–$C_6$)alkoxy.

6. The compound according to claim 5, wherein when the aryl group is disubstituted, the two substituents on the adjacent carbon atoms form a linking group selected from —X—$CH_2$—Y— and —X—$CH_2$—$CH_2$—Y—, where X and Y are the same or different and independently represent O, NH, S or $CH_2$.

7. The compound according to claim 1, wherein when the groups represented by $R^1$, $R^2$ or $R^3$ are multisubstituted, the substituents present on two adjacent carbons form a linking group —X—$(CR^6R^7)_n$—Y— where $R^6$ and $R^7$ represent ($C_1$–$C_8$)alkyl, X and Y are the same or different and independently represent C, O, S or NH; and n=1 or 2.

8. A compound of the formula (I) according to claim 1, wherein when the group represented by $R^4$ is substituted the substituents are selected from halogen atom; amino, cyano, hydroxy, nitro, trifluorethyl, ($C_1$–$C_6$) alkyl, or ($C_1$–$C_6$) alkoxy.

9. A compound of formula (I) according to claim 1, which is selected from 8,17-epoxy andrographolide;

3,14,19-triacetyl 8,17-epoxy andrographolide;

3,14,19-tripropionyl 8,17-epoxyandrographolide;

3,14,19-tris chloro acetyl 8,17-epoxy andrographolide;

8,17-epoxy andrographolide 3,19-acetonide;

14-methoxy 3,19-diacetyl 8,17-epoxy andrographolide;

14-cinnamoyl 3,19-dihydroxy 8,17-epoxy andrographolide;

14-cinnamoyl 3,19-dipropionyl 8,17-epoxy andrographolide;

14-[4'-methoxycinnamoyl]3,19-dipropionyl 8,17-epoxy andrographolide;

8,17-epoxy 14-[3',4'-dimethoxycinnamoyl]3,19-dipropionyl andrographolide;

14-[3',4'-methylene dioxy cinnamoyl]3,19-dipropionyl 8,17-epoxy andrographolide;

14-[N-Boc glycinyl]8,17-epoxy andrographolide;

14-[N-Boc glycinyl]3,19-dipropionyl 8,17-epoxy andrographolide;

19-trityl 8,17-epoxy andrographolide;

3-acetyl 8,17-epoxy Andrographolide;

3,14-diacetyl 8,17-epoxy Andrographolide;

14,19-diacetyl 8,17-epoxy Andrographolide;

3,14-dipropionyl 8,17-epoxy Andrographolide;

14-[4S,5R(N-1-butoxycarbonyl)-2,2-dimethyl-4-phenyl-5-oxazolidine]carbonyl-3,19-diacetyl-8,17-epoxy andrographolide; or 14-[2'-acetoxy-3'-N-acetylamino-3'-phenyl]propanoyl-3,19-diacetyl-3,17-epoxyandrographolide.

10. A process for the preparation of a compound of formula (I),

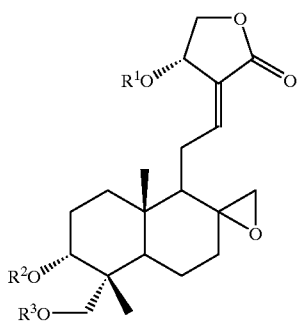

where R$^1$, R$^2$ and R$^3$ are the same or different and independently represent hydrogen or substituted or unsubstituted groups selected from alkyl, aryl, heteroaryl, aralkyl, heteroaralkyl, alkanoyl, alkenoyl, aroyl, heteroaroyl, sulfonyl group or a group —(CO)—W— R$^4$ where W represents O, S, or NR$^5$, wherein R$^5$ represents hydrogen or (C$_1$–C$_6$) alkyl group, R$^4$ represents substituted or unsubstituted groups selected from alkyl, aryl, aroyl, or aralkyl or R$^2$ and R$^3$ together form a substituted or unsubstituted 3 to 7 membered cyclic structure containing carbon and oxygen atoms; its stereoisomers, its polymorphs, its salts, or its solvates which comprises the steps of:

(i) epoxidizing andrographolide of formula (II)

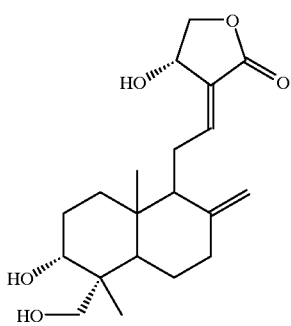

to form a compound of formula (VII),

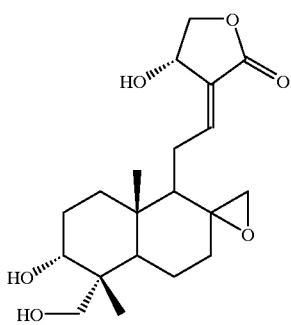

(ii) reacting the compound of formula (VII) with R$^1$—L, R$^2$—L and R$^3$—L where R$^1$, R$^2$ and R$^3$ are as defined above and L represents a leaving group to produce a compound of formula (I), and if desired, (iii) protecting the hydroxy groups present on carbons 3 or 19 or 3 and 19 together in the compound of formula (VII) with a protecting group to produce a compound of formula (VIII),

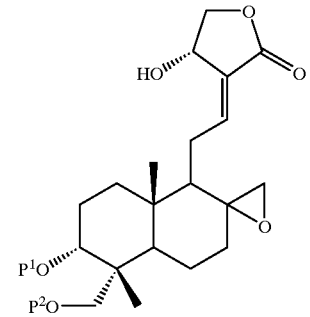

where P$^1$ and P$^2$ may be same or different and represent hydrogen, an ester, trityl, t-butyl dimethyl silyl, pivaloyl; or together form methylene dioxy, acetonide, or benzilidine;

(iv) reacting the compound of formula (VIII) defined above with compound of formula (IX)

$$R^1\text{—L} \quad (IX)$$

where R$^1$ and L are as defined above, to produce a compound of formula (X),

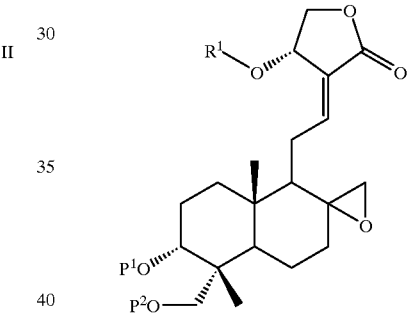

where R$^1$, P$^1$ and p$^2$ are as defined above, (v) deprotecting the compound of formula (X) to produce a compound of formula (XI),

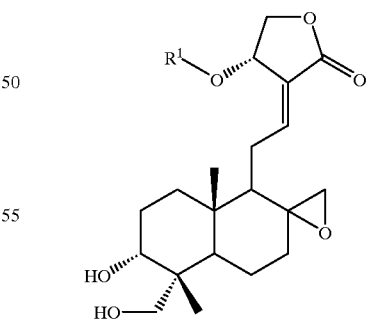

where R$^1$ is as defined above, (vi) reacting the compound of formula (XI) where R$^1$ is as defined above with R$^2$—L or R$^3$—L; or R$^2$—L, and R$^3$—L, where R$^2$, R$^3$ and L are as defined above, to produce a compound of formula (I), and if desired, (vii) converting the compound of formula (I) into its stereoisomers, salts or solvates.

11. A pharmaceutical composition which comprises an effective amount of a compound of formula (I),

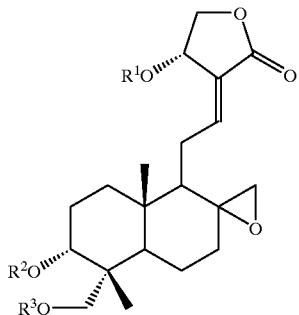

as defined in claim 1, and a pharmaceutically acceptable carrier, diluent, excipient or solvate.

12. A pharmaceutical composition as claimed in claim 11, in the form of a tablet, capsule, powder, syrup, solution or suspension.

13. A method of treating cancer, psoriasis, HSV, HIV; restenosis, atherosclerosis, viral infections, malaria, bacterial infections, immunomodulation, liver disorders, and cardiovascular disorders, diabetes, dyslipidemia, and other metabolic disorders, which comprises administering an effective amount of a compound of formula (I) as claimed in claim 1 to a patient in need thereof.

14. A method for treating insulin resistance (type II diabetes), leptin resistance, impaired glucose tolerance, dyslipidemia, body weight reduction, and disorders related to syndrome X which comprises administering an effective amount of a compound of formula (I) as claimed in claim 1 to a patient in need thereof.

15. The method according to claim 14, wherein the disorders relating to syndrome X are hypertension, obesity, insulin resistance, coronary heart disease and other cardiovascular disorders.

16. A method for preventing insulin resistance (type II diabetes), leptin resistance, impaired glucose tolerance, dyslipidemia, body weight reduction, and disorders related to syndrome X which comprises administering an effective amount of a compound of formula (I) as claimed in claim 1 to a patient in need thereof.

17. The method according to claim 16, wherein the disorders relating to syndrome X are hypertension, obesity, insulin resistance, coronary heart disease and other cardiovascular disorders.

18. A method of preventing psoriasis, restenosis, atherosclerosis, malaria, immunomodulation, liver disorders, and cardiovascular disorders, diabetes, dyslipidemia, and other metabolic disorders, which comprises administering an effective amount of a compound of formula (I) as claimed in claim 1 to a patient in need thereof.

19. A method for treating insulin resistance (type II diabetes), leptin resistance, impaired glucose tolerance, dyslipidemia, body weight reduction, and disorders related to syndrome X which comprises administering an effective amount of a compound of formula (I) as claimed in claim 9 to a patient in need thereof.

20. The method according to claim 19, wherein the disorders relating to syndrome X are hypertension, obesity, insulin resistance, coronary heart disease and other cardiovascular disorders.

21. A method for preventing insulin resistance (type II diabetes), leptin resistance, impaired glucose tolerance, dyslipidemia, body weight reduction, and disorders related to syndrome X which comprises administering an effective amount of a compound of formula (I) as claimed in claim 9 to a patient in need thereof.

22. The method according to claim 21, wherein the disorders relating to syndrome X are hypertension, obesity, insulin resistance, coronary heart disease and other cardiovascular disorders.

23. A method of treating cancer, psoriasis, HSV, HIV; restenosis, atherosclerosis, viral infections, malaria, bacterial infections, immunomodulation, liver disorders, and cardiovascular disorders, diabetes, dyslipidemia, and other metabolic disorders, which comprises administering an effective amount of a compound of formula (I) as claimed in claim 9 to a patient in need thereof.

24. A method of preventing psoriasis, HSV, HIV; restenosis, atherosclerosis, viral infections, malaria, bacterial infections, immunomodulation, liver disorders, and cardiovascular disorders, diabetes, dyslipidemia, and other metabolic disorders, which comprises administering an effective amount of a compound of formula (I) as claimed in claim 9 to a patient in need thereof.

25. A compound of formula (I),

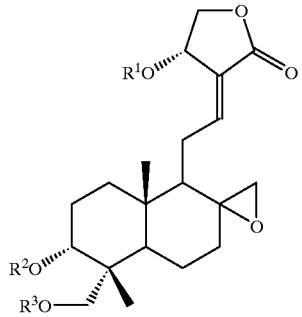

where $R^1$, $R^2$ and $R^3$ are the same or different and independently represent hydrogen or substituted or unsubstituted groups selected from alkyl, aryl, heteroaryl, aralkyl, heteroaralkyl, alkanoyl, alkenoyl, aroyl, heteroaroyl, sulfonyl group or a group —(CO)—W—$R^4$ where W represents O, S, or $NR^5$, wherein $R^5$ represents hydrogen or $(C_1-C_6)$ alkyl group, $R^4$ represents substituted or unsubstituted groups selected from alkyl, aryl, aroyl, or aralkyl or $R^2$ and $R^3$ together form a substituted or unsubstituted 3 to 7 membered cyclic structure containing carbon and oxygen atoms; its stereoisomers, its polymorphs, its salts, or its solvates prepared by the process which comprises the steps of:

(i) epoxidizing andrographolide of formula (II)

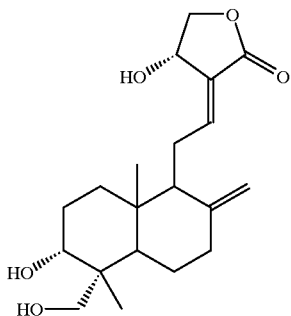

(II)

to form a compound of formula (VII),

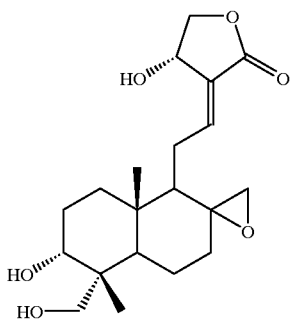

(VII)

(ii) reacting the compound of formula (VII) with $R^1$—L, $R^2$—L and $R^3$—L where $R^1$, $R^2$ and $R^3$ are as defined above and L represents a leaving group to produce a compound of formula (I), and if desired, (iii) protecting the hydroxy groups present on carbons 3 or 19 or 3 and 19 together in the compound of formula (VII) with a protecting group to produce a compound of formula (VIII),

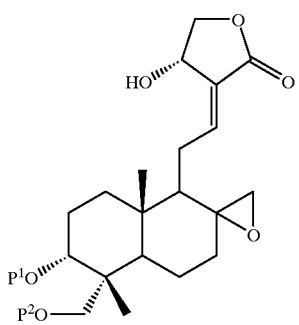

(VIII)

where $P^1$ and $P^2$ may be same or different and represent hydrogen, an ester, trityl, t-butyl dimethyl silyl, pivaloyl; or together form methylene dioxy, acetonide, or benzilidine;

(iv) reacting the compound of formula (VIII) defined above with compound of formula (IX)

$$R^1—L \qquad (IX)$$

where $R^1$ and L are as defined above, to produce a compound of formula (X), (X)

where $R^1$, $P^1$ and $P^2$ are as defined above, (v) deprotecting the compound of formula (X) to produce a compound of formula (XI), (XI)

where $R^1$ is as defined above, (vi) reacting the compound of formula (XI) where $R^1$ is as defined above with $R^2$—L or $R^3$—L; or $R^2$—L and $R^3$—L where $R^2$, $R^3$ and L are as defined above, to produce a compound of formula (I), and if desired, (vii) converting the compound of formula (I) into its stereoisomers, salts or solvates.

26. A pharmaceutical composition which comprises an effective amount of a compound of formula (I) as defined in claim 9, and a pharmaceutically acceptable carrier, diluent, excipient or solvate.

27. A pharmaceutical composition as claimed in claim 26, in the form of a tablet, capsule, powder, syrup, solution or suspension.

* * * * *